United States Patent [19]
Basler et al.

[11] Patent Number: 5,648,850
[45] Date of Patent: Jul. 15, 1997

[54] METHOD AND DEVICE FOR QUALITY CONTROL OF OBJECTS WITH POLARIZED LIGHT

[75] Inventors: Norbert Basler; Jürgen Klicker, both of Hoisdorf; Dietmar Ley, Ahrensburg, all of Germany

[73] Assignee: Basler GmbH, Ahrensburg, Germany

[21] Appl. No.: 531,692

[22] Filed: Sep. 21, 1995

[30] Foreign Application Priority Data

Sep. 27, 1994 [DE] Germany ............ 44 34 473.2

[51] Int. Cl.⁶ ..................... G01N 21/21
[52] U.S. Cl. ..................... 356/369; 356/33
[58] Field of Search ............... 356/364, 365, 356/366, 367, 369, 237, 33, 35; 250/225

[56] References Cited

U.S. PATENT DOCUMENTS

| | | | |
|---|---|---|---|
| 3,474,254 | 10/1969 | Piepenbrink et al. | 356/369 |
| 4,030,835 | 6/1977 | Firester et al. | |
| 4,381,151 | 4/1983 | Smith | 356/369 |
| 4,701,052 | 10/1987 | Schoen | 356/369 |
| 4,841,510 | 6/1989 | Yoshizawa | |
| 4,859,062 | 8/1989 | Thurn et al. | 356/371 |
| 4,908,508 | 3/1990 | Dubbeldam | 356/369 |
| 4,941,138 | 7/1990 | Chida et al. | |
| 5,131,755 | 7/1992 | Chadwick et al. | |
| 5,475,667 | 12/1995 | Kamimura et al. | |

FOREIGN PATENT DOCUMENTS

| | | |
|---|---|---|
| 326945 | 1/1989 | European Pat. Off. . |
| 3037622 | 4/1982 | Germany . |
| 3515602 | 11/1986 | Germany . |
| 3803181 | 8/1989 | Germany . |
| 2312028 | 12/1990 | Japan . |
| 3269842 | 12/1991 | Japan . |

OTHER PUBLICATIONS 1 page Abstract of DE 3515602 in English Language.
1 page Abstract of DE 3803181 in English Language.

*Primary Examiner*—Richard A. Rosenberger
*Attorney, Agent, or Firm*—Howson and Howson

[57] ABSTRACT

The invention pertains to a method and a device for carrying out the quality control of an object (10) that comprises at least one transparent layer (18). According to this method and this device, at least one light beam (41) of a light source (42) is projected onto the object (10) at an angle ($\alpha$) and is received by at least one photosensitive receiver (53). According to the invention, it is proposed that the light beam that emerges from the object be split before it is projected onto the first photosensitive receiver (53), with part of the light beam being deflected in the direction toward a second photosensitive receiver (62). This measure makes it possible to expose simultaneously two different photosensitive receivers (53, 62) so as to display different defects of an object (10).

11 Claims, 5 Drawing Sheets

METHOD AND DEVICE FOR QUALITY CONTROL OF OBJECTS WITH POLARIZED LIGHT

BRIEF SUMMARY OF THE INVENTION

The invention pertains to a method and a device for carrying out the quality control of an object that has at least one transparent layer. According to this method and this device, at least one light beam of a light source is projected onto the object at an angle land recorded by at least one photosensitive receiver. The light beam can, in principle, be reflected by a reflective layer of the object which is arranged behind the transparent layer or pass through the object, i.e., the photosensitive receiver either receives a reflected light beam or a light beam that has passed through the object. For reasons of simplicity, the following description simply refers to a light beam that is reflected by the object, passes through the object or emerges from said object. The invention in particular pertains to the optical quality control of a compact disc (CD), i.e., the following description primarily refers to a CD, but the invention is not limited to this particular type of application.

Lately, CDs have become more and more popular because these sound carriers produce a very high sound quality in domestic use. However, they are also used as pure data carriers for data processing systems because of their high data density. Last but not least, the relative insensitivity to external influences represents one additional reason for the continued popularity of Cds. Consequently, a CD unquestionably represents a mass-produced product which, however, needs to fulfill the strictest quality requirements.

There exist numerous methods for measuring the different defects that can occur during the manufacture of a CD. Due to the physical design of a CD, i.e., a transparent layer with a reflective layer arranged behind it, optical measuring methods and measuring devices which are also the object of this invention are particularly suitable for this purpose.

The initial description pertains to the design and the manufacture of a CD as well as the possible defects that can occur during the manufacturing process. A CD consists of a circular disk, in the center of which an aperture is arranged for centering it in a CD player. Viewed from the bottom, i.e., the reading side of the CD player, toward the top, the cross section of this disk consists of a transparent plastic layer that is generally manufactured of polycarbonate and contains all information in the form of pits. A metal layer that usually consists of aluminum and serves for rendering the surface of the polycarbonate layer reflective is arranged on top of the aforementioned transparent plastic layer such that the information can be read by the optical scanning system of the CD player. This very thin metal layer is protected by a coat of lacquer that is also very thin and usually hardened by means of UV light. Lettering or the like can be arranged on this coat of lacquer in order to label the CD.

Viewed in the radial direction, a CD has several concentric, annular regions that originate from the central aperture and extend outward. The region that serves for clamping the CD in the CD player is situated directly on the central aperture. A region that carries the so-called identification code that serves for conclusively identifying the CD is situated adjacent to the aforementioned region. The region that serves for storing the data is situated adjacent to the region carrying the identification code. If the CD is prerecorded to its maximum storage capacity, this region ends directly at the outer border region. Otherwise, the so-called lead-out or an image band is arranged between the outer edge region of the CD and the data region.

When manufacturing a CD, a blank is initially manufactured of polycarbonate by means of die-casting, with all information already being impressed by means of the die plate. Subsequently, one surface of the blank is provided with the metallic reflective layer by means of sputtering and sealed with the coat of lacquer. The CD is centrifuged during these processes in order to realize the uniform distribution of the aluminum layer and the coat of lacquer and to obtain the thinnest possible layer. Subsequently, the label is printed onto the CD.

It is obvious that the reflective layer and the transparent polycarbonate body need to be flawless with respect to their optical properties due to the high data density of the CD that is read in an optical fashion. The slightest defects, in particular within the data region, can cause significant interference during the reading process, i.e., unacceptable aberrations can result, in particular if the CD is used for data processing. Consequently, it is practical as well as necessary to incorporate a quality control that makes it possible to detect and classify the possible defects of a CD into the production process such that a subsequent elimination of the defective Cds or a rectification of the production process can be carried out.

The following defects can occur: holes in the reflective layer, so-called pinholes, are created by a dust particle or the like which is present on the surface before the sputtering process and are thrown outward while entraining a piece of the metallic surface during the centrifuging of the CD. Aluminum scratches occur if the dust particle remains on the surface while it is thrown outward and consequently causes additional damage to the metal layer. Underneath the metal layer, organic residues, e.g., oil stains, can lead to scanning errors. So called pimple defects are created if the polycarbonate blank is deformed on the side that is to be coated. Inclusions of foreign matter in the polycarbonate layer are called black spots. Bubbles, air inclusions or the like can also be present in the polycarbonate layer. In addition, the underside of the CD can contain lacquer splashes or scratches that are caused by mechanical influences and lead to reading errors or diminish the sound quality.

Depending on their size, these defects always cause optical aberrations that can usually be detected with conventional test equipment. However, a classification of the defects also requires that the depth of the respective defects is determined. Consequently, it is required to utilize measuring methods and measuring devices that are also known that are able to measure the defects in a three-dimensional fashion. Depending on the data density, it is, at least within the data region, also required to carry out the tests with a high inspection level, i.e., a local resolution within the range between 30 µm and 50 µm needs to be attained. Outside of the data region, only defects that influence the optical appearance of the CD are important. In this case, a lower inspection level, e.g., with a local resolution of approximately 200 µm, which corresponds to that of the human eye, would suffice.

In addition, optical distortions in the CD can be caused, for example, due to a convex or concave deformation of the CD. Internal stresses in the polycarbonate layer also lead to reading errors because polycarbonate is an optically active material under tension, i.e., birefrigence occurs. This causes the usually polarized light of the scanning laser in the CD player to be subjected to an undesired change in polarization due to this accidental birefrigence. In addition, defects in the microstructure of the polycarbonate layer frequently lead to reading errors. The reason for these so-called clouds frequently lies in the die plate, i.e., one must assume that the system does not operate properly if such a cloud is present.

In order to detect the first-mentioned group of defects, there exist measuring methods and measuring devices in which a linear light beam is projected onto the underside at an acute angle, reflected on the reflective layer and recorded by a so-called line camera. The defect appears in the camera in the form of a dark spot. The CD carries out one revolution during the test procedure such that the entire CD can be illuminated and examined as to the presence of possible defects. Due to the distinct geometry and the predetermined revolution of the CD, one can simultaneously draw conclusions as to the depth of a defect since the same defect appears twice at the same location during the revolution, i.e., the defect lies in the incident light beam as well as in the emerging light beam. However, it is currently not possible to reliably detect the presence of a cloud with conventional measuring methods.

However, it is also possible to test the blank of the CD by means of transillumination before the sputtering process is carried out. In this case, the light source and the photosensitive receiver are situated on opposite sides of the CD.

In order to detect internal stresses, the light beam is polarized in linear fashion via a polarizing filter behind the light source, with a linear polarizing filter also being arranged in front of the camera. The polarizing filters are usually arranged in such a way that they are turned relative to one another by 90°. When testing a flawless CD, i.e., a CD without internal stresses, the camera remains completely dark because the polarized light did not change while passing through the polycarbonate layer. Otherwise, the brightness observed in the camera represents a measure of the internal stresses.

However, if the illumination is realized with light that is linearly polarized, it is not possible to detect all internal stresses that can lead to scanning errors. The reason for this can be seen in the fact that the internal stress causes a birefringence with a privileged direction that might not be detected by light that is linearly polarized depending on the direction of polarization. Consequently, it can occur that a CD which is classified as flawless in a conventional measuring method still has internal stresses.

Deformations of a CD are determined by projecting a point source light beam that in most cases originates from a semiconductor light source onto the underside of the CD and reflecting said light beam in the direction of a position-sensitive photodiode. Photodiodes of this type can, for example, be realized in the form of four-quadrant diodes. When testing a flat CD, the light beam is reflected onto a certain region of the photodiode. When testing a CD that is deformed in convex or concave fashion, for example, the light beam is deflected and illuminates a different quadrant of the photodiode. In this case, the extent of the deflection can be used as a measure of the extent of the deformation. However, one disadvantage of this method can be seen in that the CD is only tested along one diameter. Hat-shaped or bead-shaped deformations cannot be detected if the light beam is projected onto an otherwise flat CD.

One additional disadvantage of known methods is that several steps are required for different measuring problems. Among other things, the reason for this can be seen in the fact that, when testing a flawless object, the photosensitive receiver remains dark during a known birefringence test and consequently is not available for additional evaluations.

The invention is based on the objective of developing a measuring method and a measuring device which make it possible to detect several measuring problems with only one photosensitive receiver. In addition, the invention should make it possible to display internal stresses in the examined object independent of the privileged direction of the birefringence.

According to the invention, this objective is attained by the fact that the light beam is polarized within at least one wavelength range after the light source, and that the light that emerges from the object passes through a corresponding polarization device before it is projected onto the photosensitive receiver, with said polarization device being aligned such that the light passes if a flawless object is tested, i.e., an object that is flawless with respect to birefringence. This measure provides the advantage that additional defect phenomena can be displayed and evaluated on the photosensitive receiver, namely even if the object is flawless with respect to birefringence. In this case, it is possible to proceed such that the portion, the polarization type of which corresponds with the polarization type of the emitted light, is filtered out of the light beam before it is projected onto the photosensitive receiver.

It is, in principle, possible to realize a linear polarization of the light by means of a corresponding polarizing filter. However, it is also possible to circularly polarize the light beam within at least one wavelength range by means of a linear polarizing filter and a $\lambda/4$ plate. In this case, a corresponding arrangement of the phase delay plate and the linear polarizing filter is provided in front of the photosensitive receiver. It was unexpectedly demonstrated that light that is circularly polarized makes it possible to display the defects in the microstructure, the so-called clouds, in a superior fashion and distinctly classify said defects on the photosensitive receiver.

In addition, it was demonstrated that light that is circularly polarized is also able to display internal stresses independent of the privileged direction of the birefringence. According to the invention, it is proposed that the portion, the polarization type of which corresponds with the polarization type of the emitted light, is filtered out of the light beam before it is projected onto at least one photosensitive receiver. In this case, it can be practical with respect to a high-contrast display if the wavelength range, the wavelength of which corresponds to the wavelength range of the emitted light that is circularly polarized, is filtered out of the light beam before it is projected onto at least one photosensitive receiver. This measure makes it possible to display internal stresses independent of the privileged direction of the birefringence on the respective photosensitive receiver or the monitor that is connected with said photosensitive receiver.

It is practical if the light beam is elliptically polarized by means of a linear polarizing filter and a phase delay plate, e.g., a $\lambda/4$ plate. In this case, a corresponding arrangement of the phase delay plate and the linear polarizing filter is provided in front of the photosensitive receiver. This measure provides the advantage that a possible change in polarization which is caused by the reflection on the metal reflective layer can be compensated.

At this point, it should be emphasized that the description only refers to the display of a defect on or by the photosensitive receiver for reasons of elucidation, i.e., the defect is recorded by the photosensitive receiver and graphically illustrated on a corresponding display element, e.g., a monitor that is connected with the photosensitive receiver.

According to one additional embodiment of the invention, it is proposed that the reflected light beam or the light beam that passes through the object be split before it is projected onto the photosensitive receiver, with part of the light beam being deflected in the direction toward a second photosensitive receiver. This measure provides the advantage that two photosensitive receivers which, for example, are particularly practical for displaying different defects can be exposed by one light source, i.e., in one step.

According to one practical embodiment of the invention, it is proposed that the reflected light beam or the light beam that passes through the object be split by means of a beam splitter that is arranged between the first photosensitive receiver and the object, with part of the light beam being deflected in the direction toward the second photosensitive receiver. This measure makes it possible to attain a simpler and more compact design of the device required for carrying out the test method.

In addition, it is possible that part of the light beam that is reflected by the object be reflected by a partially transparent mirror such that said light beam is projected onto the object in the opposite direction at an angle that is essentially identical to the angle of incidence, reflected and projected onto a beam splitter that is arranged between the object and the light source, with part of the light beam being deflected in the direction of the second photosensitive receiver in said beam splitter. This progression of the light beam provides the advantage that the contrast on the second photosensitive receiver can be increased because the incident light beam as well as the light beam reflected by the partially transparent mirror pass over the CD while said CD remains in the same position, i.e., the CD does not revolve. Consequently, defects that have a lower contrast, e.g., large-surface or stochastic defects that only cause a minute diminishing of the light beam if it passes over the object once, can also be detected because these defects now diminish the light beam twice.

It is practical for the light beam to illuminate the object in a linear fashion. In this case, at least one photosensitive receiver can be realized in the form of a line camera. Due to this measure, the measuring time can be reduced and the other defects of the first-mentioned group of defects can be detected simultaneously.

However, it is also practical if at least one photosensitive receiver is realized in the form of a matrix camera. A matrix camera can display the possible deformations in a CD in a superior fashion. If such a deformation exists, a linear illumination of the CD is displayed as a correspondingly curved line in the matrix camera that has a two-dimensional receiver. Consequently, it is also possible to detect hat-shaped or bead-shaped deformations in a CD.

In addition to the internal stresses, it is also possible to display possibly existing deformations because the polarization device used for filtering out the polarization type is aligned and adjusted such that the passage of the light is ensured if no birefringence is present. Conclusions as to possible deformations in the CD can be drawn from the progression of the recorded, originally linear light beam. Consequently, it is possible to solve two different measuring problems in one step.

It is particularly practical if the first photosensitive receiver is realized in the form of a matrix camera that is arranged behind the partially transparent mirror and the second photosensitive receiver is realized in the form of a line camera.

In this case, it is, in principle, practical if the corresponding, reverse polarization device and/or the color filter is/are arranged in front of the matrix camera. In such an arrangement it is possible to record the internal stresses and the deformations with the matrix camera while the line camera detects the other defects.

In addition, it is possible that the illumination takes place at least partially along a beam that originates from the central axis when testing a rotationally symmetrical object. It is also practical if the measurements are carried out during at least one complete revolution of the object, with all measured values being processed in an electronic data processing system so as to generate an essentially complete picture of the tested object. This measure significantly simplifies the evaluation of defects.

The device for carrying out the quality control of an object that comprises at least one transparent layer, in particular a compact disc (CD), is provided with a light source for generating at least one light beam that is projected onto the object at an angle as well as at least one photosensitive receiver for recording the reflected light beam or the light beam that passes through the object. According to the invention, it is proposed that at least one polarization device be arranged between the light source and the object, and that a corresponding polarization device, which is aligned such that light passes if an essentially flawless object with respect to the birefringence is tested, be arranged in front of the photosensitive receiver. This device in particular can be advantageously utilized for carrying out the previously described method. Naturally, it is also possible to use a light source that generates light that is already polarized in a linear fashion, e.g., by utilizing a laser.

In this case, it is practical if each polarization device comprises a linear polarizing filter and a phase delay plate. Depending on the angular position of the linear polarizing filter relative to the phase delay plate, e.g., a λ/4 plate, it is possible to generate light that is elliptically or circularly polarized. This type of polarization is filtered out in front of the photosensitive receiver by the corresponding polarization device. If a laser is used as the light source that emits light that is linearly polarized, the polarization device arranged behind the light source only needs to comprise a phase delay plate.

According to one additional embodiment of the invention, it is proposed that at least one element be provided that splits the light beam that is reflected by the object or passes through the object before it is projected onto the first photosensitive receiver and deflects part of said light beam in the direction of a second photosensitive receiver. In this case, the element for splitting the light beam can comprise a beam splitter arranged between the object and the first photosensitive receiver. However, it is also possible that the element for splitting the light beam comprises a beam splitter arranged between the object and the light source. In this case, a partially transparent mirror, which is aligned such that the light beam is reflected onto the object in the opposite direction, is arranged in front of the first photosensitive receiver.

In order to detect internal stresses independent of the privileged direction of the birefringence, it is additionally proposed that a polarization device be installed in the opposite direction in front of at least one photosensitive receiver so as to filter out the portion of the incident light, the polarization type of which corresponds with the polarization type of the emitted light. The polarization device can, for example, comprise a phase delay plate and a linear polarizing filter viewed in the beam direction. In this case, the respective phase delay plates arranged in front of the photosensitive receiver and after the light source operate with the same wavelength. It is advantageous with respect to a high-contrast display if a color filter, the wavelength of which corresponds with the wavelength of the light that is circularly or elliptically polarized, is arranged in front of the phase delay plate situated in front of the camera.

If a partially transparent mirror is used, it is practical to realize said mirror in the form of an interference filter, the wavelength of which corresponds with the wavelength of the light that is circularly or elliptically polarized. Consequently, the remaining portion of the light is reflected such that the light quantity available for the other photosensitive receivers is diminished less intensely.

In any case, it is practical if the light source generates a linear light beam. In this case, at least one photosensitive receiver can be realized in the form of a line camera. However, it is also possible to realize at least one photosensitive receiver in the form of a matrix camera.

In addition, it is practical if at least one photosensitive receiver is connected with a data processing system due to the large amount of picture information to be processed.

The previous description pertained to different embodiments that, in particular, refer to the display of internal stress and operate with two photosensitive receivers. Naturally, these embodiments can also pertain to devices that are only provided with one photosensitive receiver.

BRIEF DESCRIPTION OF THE DRAWINGS

The invention is described in detail below with reference to the schematic figures. Shown are.

DETAILED DESCRIPTION

Figure 1:
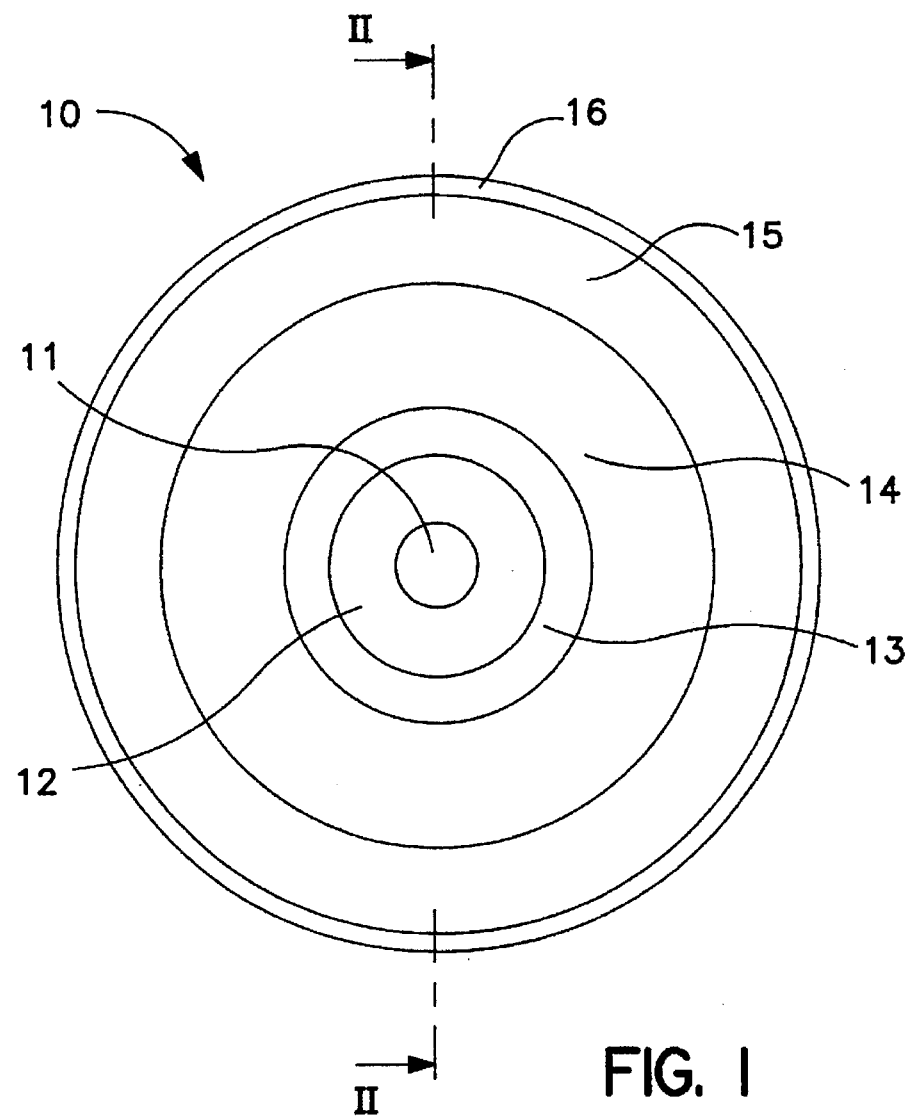
FIG. 1, a top view of a compact disc.
Figure 2:
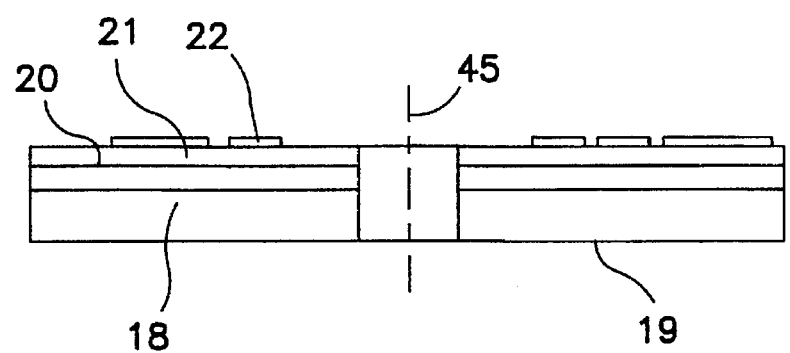
FIG. 2, a cross section through a compact disc along line II—II in FIG. 1.

FIGS. 1 and 2 schematically illustrate the design of a CD 10. The CD 10 comprises different regions in the radial direction as shown in FIG. 1. Looking from the inside out, one can observe the central aperture 11 for centering the CD in the CD player and the inner edge region 12 for clamping the CD in the CD player. A region 13 that carries the identification code and is surrounded by the data region 14 is situated adjacent to the aforementioned inner edge region. Depending on the amount of recorded information, a lead-out 15 or the outer edge region 16 of the CD are situated adjacent to the data region 14.

Viewed in the axial direction from the bottom up (FIG. 2), the CD 10 comprises a transparent polycarbonate layer 18 that is provided with a metal layer 20 on the side situated opposite to the underside 19. Consequently, a reflective surface is created such that the data that is stored within the polycarbonate layer in the form of pits (not shown) can be scanned by optical means in the CD player from the underside 19. A coat of lacquer 21 seals the side of the metal layer 20 that is opposite to the polycarbonate layer 18 with a color layer 22 in the form of a label printed on said coat of lacquer.

Figure 3:
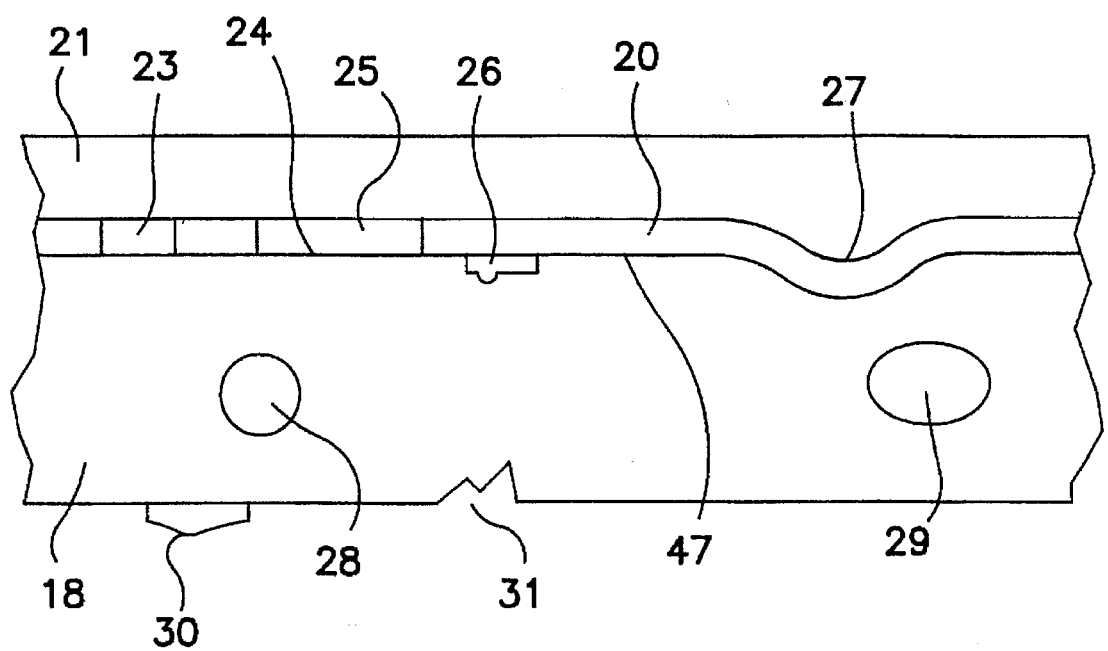
FIG. 3, a schematic representation of the possible defects in a compact disc.

FIG. 3 shows the possible defects that might occur during the manufacture of a CD and that can be displayed by means of conventional measuring methods. Reference numeral 23 identifies so-called pinholes which are caused by dust particles that become located on the surface 24 of the polycarbonate blank, separate from the surface, while the CD is centrifuged during the sputtering process and which entrain a piece of the metal layer 20 during this process. The so-called aluminum scratches 25 are created in the same fashion, but the dust particle initially continues to travel outward on the surface 24. The oil stains 26 represent organic residues on the surface 24 of the polycarbonate layer 18 of the CD 10. A so-called pimple defect 27 is caused by a deformation of the polycarbonate blank 18. Black spots 28 due to inclusions of foreign matter or bubbles 29 due to gas inclusions can also be present within the polycarbonate layer 18. Lacquer splashes 30 or scratches 31 caused by external mechanical influences can occur on the underside 19 of the polycarbonate layer.

These defects diminish the intensity of the test light beam such that black or dark areas become visible at the respective locations of the graphical representation. The other defects which were described previously cannot be easily graphically represented, but partially cause a diminished exposure of the photosensitive receiver or a deflection of the test light beam.

Figure 5:
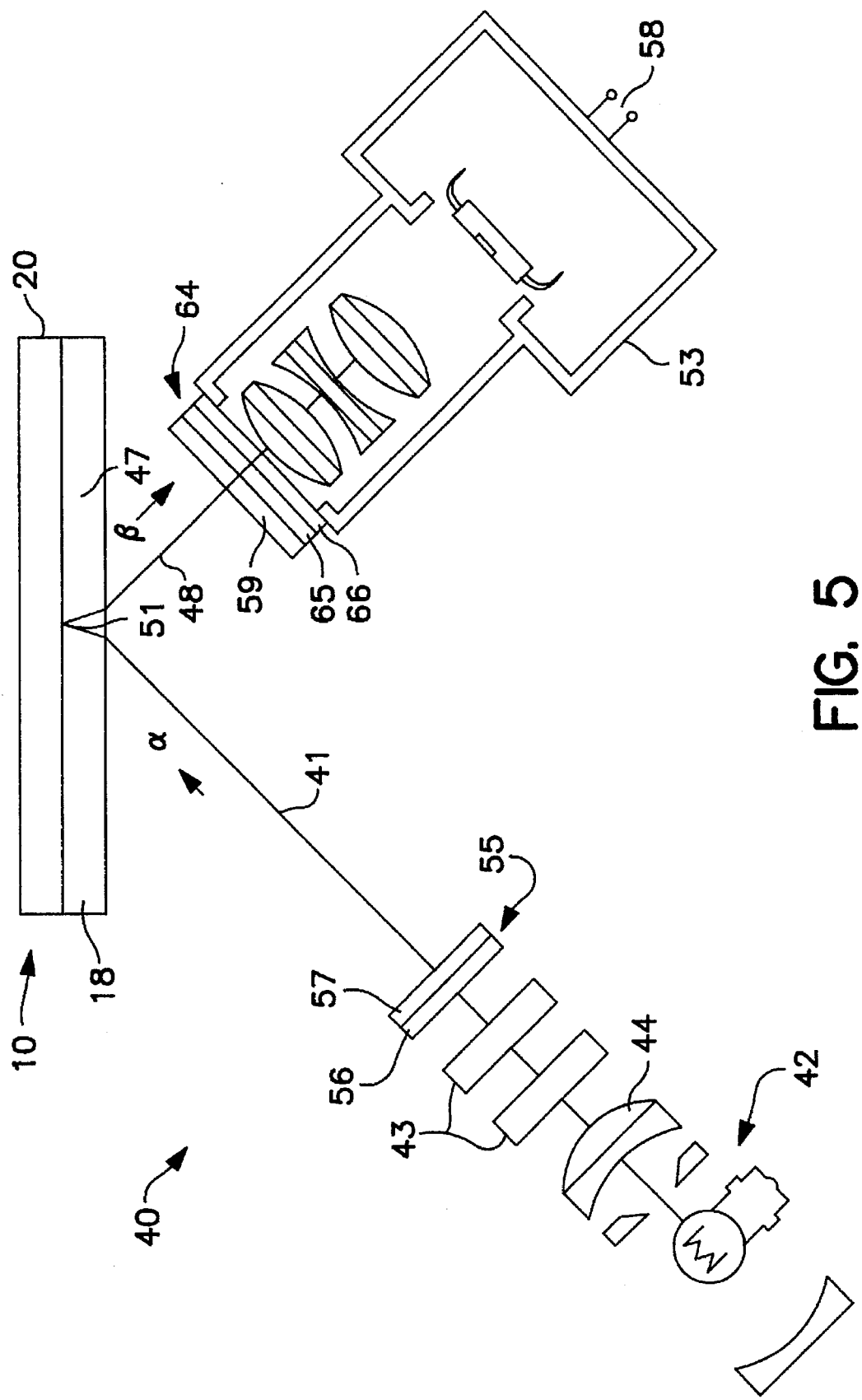
FIG. 5, a schematic representation of the path of the light beam while testing a deformed CD, FIG. 6, a device according to the invention, and FIG. 7, an additional embodiment of a device according to the invention.

FIG. 5 schematically illustrates a device 40 for carrying out the quality control of CDs 10. This illustration is limited to the path of the light beam 41 because a person skilled in the art is familiar with the required design, the angles to be observed, etc.

Figure 4:
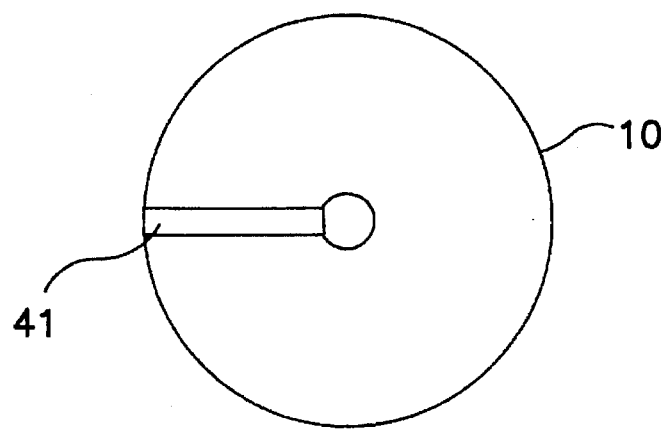
FIG. 4, a top view of a CD that is illuminated by a light beam.

The device 40 comprises a light source 42 that, for example, can be realized in the form of a conventional halogen lamp. A light beam 41 that has a linear shape relative to the surface of the CD 10 and is projected onto the underside 19 of the CD 10, i.e., the reading side, in the form of a beam that originates radially from the central axis 45, can be generated with an arrangement of different, generally known diaphragms and lenses 43, 44. During the test, the CD revolves around this central axis 45. The linear illumination of the CD 10 is illustrated in FIG. 4. Naturally, it is also possible that this light beam extends over the entire diameter of the CD 10. In this case, only one-half revolution of the CD 10 would be required for carrying out a comprehensive test.

A polarization device 55 that comprises a linear polarizing filter 56 and a phase delay plate 57, e.g., a $\lambda/4$ plate, in order to circularly or elliptically polarize at least one wavelength of the light beam 41 is provided between the light source 42 and the CD 10 in the direction of the light beam 41. This means that at least one wavelength of the emitted light is polarized correspondingly. The light beam 41 is projected on the underside 19 of the transparent layer 18 of the CD, i.e., the polycarbonate layer, and refracted at this location in accordance with the optical properties of this layer 18. In this case, the angle of incidence $\alpha$ is chosen such that no total reflection occurs on the underside 19 of the polycarbonate layer 18, e.g., between 30° and 60°. However, it is, in principle, also possible that the angle of incidence amounts to 90°, but an acute angle of incidence is preferred. The light beam 41 is reflected on the reflective surface 47 formed by the metal layer 20 and, after being refracted correspondingly, emerges from the polycarbonate layer 18 at the same angle of reflection $\beta$.

A first photosensitive receiver 53 is arranged in the path of the reflected light beam 48. Depending on the design of the device and the type of defect to be detected, the photosensitive receiver can be realized in the form of a line camera or matrix camera.

In the embodiment shown in FIG. 5, a polarization device 64 that comprises a phase delay plate 65, e.g., a $\lambda/4$ plate, and a linear polarizing filter 66 viewed in the beam direction is arranged in the opposite direction between the CD 10 and the photosensitive receiver 53. In addition, a color filter 59 can be arranged in front of the phase delay plate 65. The phase delay plate 57, phase delay plate 65 and the color filter 59 have the same wavelength. Consequently, internal stresses can be displayed on the photosensitive receiver 53 independent of the privileged direction of the birefringence. In this case, the linear polarizing filter and the phase delay plates after the light source and in front of the photosensitive receiver are aligned such that the light passes if a CD that is flawless with respect to the birefringence is tested.

It is, in principle, possible to detect internal stresses with any type of polarized light. In order to allow the universal utilization of the test method, it is proposed that the polarizing filters which are respectively arranged in front of the light source and in front of the photosensitive receiver are aligned such that the light, preferably the maximum quantity of light, passes if a flawless object is tested such that other defect phenomena can also be observed in the respective photosensitive receiver in addition to the birefringence. Depending on the significance of possible defects of the object, the line camera or even the matrix camera can, for example, be provided with the corresponding polarizing filter.

The previous description primarily referred to the utilization of light that is linearly or circularly polarized. Naturally, it is also possible to generate light that is elliptically polarized by correspondingly aligning the linear polarizing filter and the phase delay plate ($\lambda/4$ plate). This provides the advantage that a change in the direction of polarization caused by the metal reflective layer can be compensated. A change in the direction of polarization due to reflection is a physically known process, i.e., the required angle between the linear polarizing filter and the phase delay plate can be easily determined. In this case, turning by an angle that deviates by 45° is chosen such that possible birefringences can be displayed independent of the privileged direction. In this case, the phase delay plate and the polarizing filter in front of the photosensitive receiver are correspondingly aligned relative to one another.

The polarization device 64 arranged in front of the photosensitive receiver is not absolutely imperative for displaying the defects in the microstructure, the so-called clouds. In this case, the photosensitive receiver 53 can, for example, be realized in the form of a line camera. The line camera comprises a customary linear receiver that is at least partially exposed by the linear light beam. Possible defects of the CD 10 are displayed in the form of corresponding dark spots or spots that are illuminated less intensely.

Figure 6:
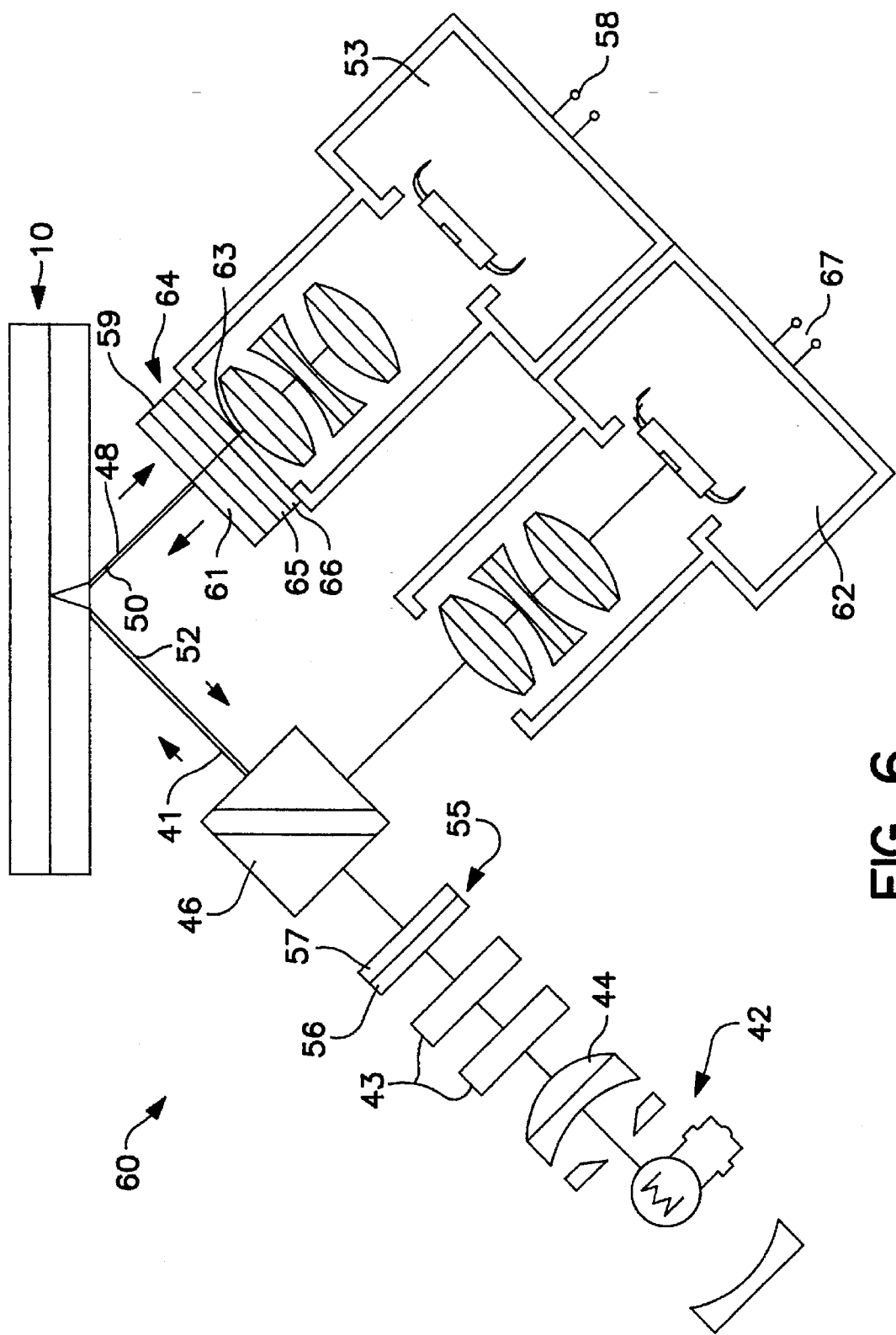

FIG. 6 shows one additional development of this embodiment of the invention which at least partially corresponds to the embodiment according to FIG. 5. Consequently, identical components or elements are identified by the same reference numerals.

In the device 60 shown in FIG. 6, a partially transparent mirror 61 is arranged in front of the photosensitive receiver 53. In this arrangement, only part 63 of the light beam 48 that is reflected by the reflective surface 47 of the CD 10 passes toward the first photosensitive receiver 53 while the other part is reflected in exactly the opposite direction by the partially transparent mirror 61 such that a light beam 50 that extends opposite the reflected light beam 48 is created. In order to prevent any misunderstanding, it should be emphasized that the different light beams are only illustrated adjacent to one another for reasons of elucidation. If the optical system is adjusted correctly and the CD 10 is not deformed, the light beams extend at least approximately on top of one another.

This light beam 50 is again refracted in accordance with the optical properties of the transparent layer 18 and reflected on the reflective surface at approximately the same point 51 at which the incident light beam 41 has already been reflected. The emerging light beam 52 is projected onto the beam splitter 46 that is arranged between the CD 10 and the light source. Part of the light beam is deflected at this location, e.g., by 90°. In this case, the beam splitter 46 is designed such that the original light beam 41 that is emitted by the light source 42 is not deflected. A second photosensitive receiver 62 is arranged behind the beam splitter 46 viewed in the direction of deflection.

This device makes it possible to simultaneously expose two cameras, i.e., during one test procedure, with only one light source and consequently only one linear light beam 41 such that different defects that require different types of cameras can be detected. It is practical to provide a more intense light source 42 because the light beam 41 is split by the partially transparent mirror 61 and the beam splitter 46.

It is, for example, possible to detect deformations of the CD 10 with the first photosensitive receiver 53, e.g., a matrix camera. It is advantageous if the polarization device 64 is arranged after the partially transparent mirror such that possibly existing internal stresses can also be displayed in addition to the deformation of the CD 10. In this case, it is practical if the partially transparent mirror is realized in the form of an interference filter. The color filter 45 can be omitted in this instance.

Such a polarization device is, however, not arranged in front of the second photosensitive receiver 62, e.g., a line camera. In addition to the defects of the first-mentioned group of defects, the so-called clouds can also be displayed in this line camera. Due to the arrangement according to FIG. 6, the light beam passes over the CD 10 twice before it is projected onto the photosensitive receiver 62, namely once in the form of the original light beam 41 and once in the form of the light beam 50 that is reflected by the partially transparent mirror 61, in one measuring position, i.e., the CD 10 does not carry out an additional revolution. It is quite obvious that this measure makes it possible to also display low-contrast defects since the same light beam is diminished twice by the same defect such that the contrast is increased as compared to the adjacently extending undisturbed beams.

Figure 7:
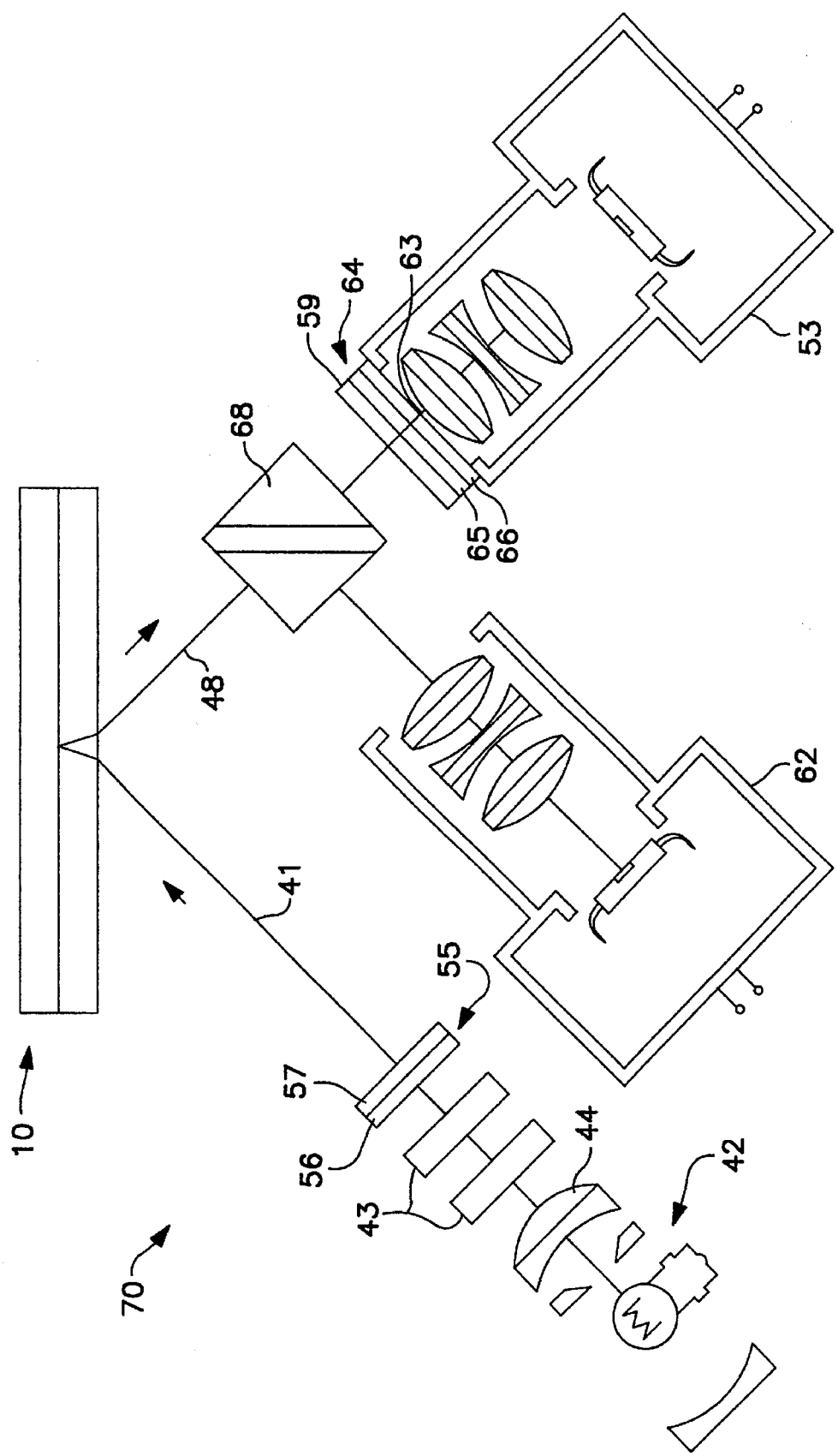

FIG. 7 shows one additional embodiment of the invention which at least partially corresponds with the embodiments according to FIGS. 6 and 7 [sic]. Consequently, identical components or elements are identified by identical reference numerals. In the device 70 according to this embodiment, a beam splitter 68 is arranged between the first photosensitive receiver 53 and the CD 10. The second photosensitive receiver 62 is arranged in the direction of deflection of the beam splitter. In this embodiment, the light beam 48 that is reflected by the object 10 is directly split. This provides the advantage that the light is no longer diminished quite as intensely due to the otherwise repeated passage of the light beam over the CD 10. In other respects, the previous description of the embodiment according to FIG. 6 applies. This particular embodiment can be practical with certain spatial arrangements of the measuring device. It is, in particular, also possible to expose two different cameras that serve for detecting different defects with only one light beam.

In the two embodiments according to FIGS. 6 and 7, it is also possible to realize the beam splitter 46, 68 in the form of a polarizing beam splitter. In this case, the λ/4 plate 57 would be arranged behind the beam splitter 46 in order to generate the circularly polarized light. Depending on the alignment and the arrangement of the polarization beam splitter, the light passes through the thusly formed polarizing filter of both photosensitive receivers. However, this can be easily taken into consideration during an evaluation.

The embodiments shown in the figures only refer to devices in which the light beam is reflected on the reflective surface. Naturally, it is also possible to realize a design in which the light beam passes through the transparent blank. In this case, the corresponding photosensitive receiver and, if applicable, the element for splitting the beam needs to be arranged on the side of the CD that is situated opposite the light source.

We claim:

1. A method for optically detecting a double refraction phenomenon in an optical disc or the like which has a transparent layer, the double refraction phenomenon being caused by internal stresses within the optical disc, comprising the steps of:

projecting a light beam onto the optical disc such that said light beam is reflected by the optical disc, said light beam having at least one wavelength range thereof elliptically polarized by a first phase delay plate before being projected onto the optical disc;

filtering said light beam with a polarization device after said light beam is reflected by the optical disc; and exposing said light beam to a photosensitive receiver after said light beam is filtered by said polarization device;

wherein said polarization device filters a polarized part of said light beam which corresponds in polarization to that of said light beam projected onto the optical disc;

wherein said polarization device comprises a second phase delay plate and a linear polarization filter; and wherein said polarization device is arranged with respect to said light beam such that said light beam is transmitted through said polarization device only if the transparent layer of the optical disc is essentially flawless without any double refraction phenomenons;

whereby said light beam exposed to said photosensitive receiver which indicates a lack of a double refraction phenomenon is useable to simultaneously detect for other error phenomenon in the optical disc.

2. Method according to claim 1, wherein said light beam reflected by the optical disc has a wavelength range which corresponds to said at least one wavelength range of said elliptically polarized light beam projected onto the optical disc; and wherein said wavelength range of said light beam reflected by the optical disc is filtered by said polarization device.

3. A method according to claim 1, wherein the optical disc has a metallic reflective coating which is located behind the transparent layer and which reflects said light beam; wherein said elliptically polarized light beam projected onto the optical disc has a polarization direction which is changed when said light beam is reflected off of the metallic reflective coating of the optical disc; and further comprising the step of aligning said first phase delay plate in a manner to compensate for said change of said polarization direction.

4. A method according to claim 1, wherein said light beam projected onto the optical disc extends linearly across the transparent layer of the optical disc, and wherein said photosensitive receiver is a matrix camera.

5. A method for optically detecting a double refraction phenomenon in an optical disc or the like which has a transparent layer, the double refraction phenomenon being caused by internal stresses within the optical disc, comprising the steps of:

projecting a light beam onto the optical disc such that said light beam is reflected by the optical disc, said light beam having at least one wavelength range thereof circularly polarized by a λ/4 plate before being projected onto the optical disc;

filtering said light beam with a polarization device after said light beam is reflected by the optical disc; and exposing said light beam to a photosensitive receiver after said light beam is filtered by said polarization device;

wherein said polarization device filters through a polarized part of said light beam which corresponds in polarization to that of said light beam projected onto the optical disc;

wherein said polarization device comprises a λ/4-plate and a linear polarization filter; and wherein said polarization device is arranged with respect to said light beam such that said light beam is transmitted through said polarization device only if the transparent layer of the optical disc is essentially flawless without any double refraction phenomenons;

whereby said light beam exposed to said photosensitive receiver which indicates a lack of a double refraction phenomenon is useable to simultaneously detect for other error phenomenon in the optical disc.

6. A method according to claim 5, wherein said light beam reflected by the optical disc has a wavelength range which corresponds to said at least one wavelength range of said circularly polarized light beam projected onto the optical disc; and wherein said wavelength range of said light beam reflected by the optical disc is filtered by said polarization device.

7. Device for optically detecting a double refraction phenomenon in an optical disc or the like which has a transparent layer, the double refraction phenomenon being caused by internal stresses within the optical disc, comprising:

a light source for projecting a polarized light beam onto the optical disc such that said polarized light beam is reflected by the optical disc;

a first phase delay plate for elliptically polarizing at least one wavelength range of said polarized light beam before said polarized light beam is projected onto the optical disc;

polarization means for filtering said polarized light beam after said light beam is reflected by the optical disc; and a photosensitive receiver arranged to be exposed to said polarized light beam after said light beam is filtered by said polarization means;

wherein said polarization means filters a polarized part of said polarized light beam which corresponds in polarization to that of said polarized light beam projected onto the optical disc;

wherein said polarization means comprises a second phase delay plate and a linear polarization filter; and wherein said polarization means is arranged with respect to said polarized light beam such that said polarized light beam is transmitted through said polarization means only if the transparent layer of the optical disc is essentially flawless without any double refraction phenomenons;

whereby said polarized light beam exposed to said photosensitive receiver which indicates a lack of a double refraction phenomenon is useable to simultaneously detect for other error phenomenon in the optical disc.

8. A device according to claim 7, wherein said first phase delay plate is a λ/4-plate that is angularly positionable to circularly polarize said at least one wavelength range of said polarized light beam, and wherein said second phase delay plate is a λ/4-plate adapted to filter said polarized part of said polarized light beam which corresponds in polarization to that of said polarized light beam projected onto the optical disc.

9. A device according to claim 8, further comprising a color filter arranged in front of said photosensitive receiver and having a wavelength range which corresponds to said at least one wavelength range of said circularly polarized light beam.

10. A device according to claim 7, further comprising a color filter arranged in front of said photosensitive receiver and having a wavelength range which corresponds to said at least one wavelength range of said elliptically polarized light beam.

11. A device according to claim 7, wherein said light source emits said polarized light beam in a manner that said polarized light beam is projected linearly across the transparent layer of the optical disc; and wherein said photosensitive receiver is a matrix camera.

* * * * *